United States Patent
Dailey et al.

(10) Patent No.: US 7,504,373 B2
(45) Date of Patent: Mar. 17, 2009

(54) SURFACTANT COMPOSITION AND METHOD OF FORMING

(75) Inventors: James S. Dailey, Grosse Ile, MI (US); Ernst Lippert, Oak Ridge, NJ (US); Sridhar Iyer, Matthews, NC (US); Ulrich Steinbrenner, Neustadt (DE); Christoffer Kieburg, Maxdorf (DE); Juergen Tropsch, Roemerberg (DE); Richard Baur, Mutterstadt (DE); Soeren Zimdahl, Schriesheim (DE)

(73) Assignee: BASF Corporation, Florham Park, NJ (US)

( * ) Notice: Subject to any disclaimer, the term of this patent is extended or adjusted under 35 U.S.C. 154(b) by 105 days.

(21) Appl. No.: 11/677,824

(22) Filed: Feb. 22, 2007

(65) Prior Publication Data

US 2007/0225189 A1  Sep. 27, 2007

(30) Foreign Application Priority Data

Feb. 22, 2006  (EP) .................................. 06110269

(51) Int. Cl.
- C11D 1/72 (2006.01)
- C11D 1/825 (2006.01)
- C11D 3/20 (2006.01)
- C11D 11/04 (2006.01)

(52) U.S. Cl. ............... 510/421; 510/342; 510/360; 510/365; 510/475; 510/505; 510/524; 510/525

(58) Field of Classification Search ............ 510/342, 510/360, 365, 421, 475, 505, 524, 525
See application file for complete search history.

(56) References Cited

U.S. PATENT DOCUMENTS

| | | | |
|---|---|---|---|
| 3,953,352 A | 4/1976 | Mizutani et al. | |
| 4,013,579 A | 3/1977 | Nakasone et al. | |
| 4,043,931 A | 8/1977 | Jeffrey et al. | |
| 4,269,723 A | 5/1981 | Barford et al. | |
| 4,501,680 A | 2/1985 | Aszman et al. | |
| 4,587,030 A | 5/1986 | Casey | |
| 4,722,802 A | 2/1988 | Hutchings et al. | |
| 4,820,449 A | 4/1989 | Menke et al. | |
| 4,911,858 A | 3/1990 | Bunczk et al. | |
| 4,911,859 A | 3/1990 | Bunczk et al. | |
| 4,999,869 A | 3/1991 | Holland et al. | |
| 5,049,302 A | 9/1991 | Holland et al. | |
| 5,340,495 A | 8/1994 | Mulcahy et al. | |
| 5,342,550 A | 8/1994 | Burke et al. | |
| 5,514,288 A | 5/1996 | Holland et al. | |
| 5,562,850 A | 10/1996 | Woo et al. | |
| 5,608,118 A | 3/1997 | Dahlgren et al. | |
| 5,661,121 A | 8/1997 | Dahlgren et al. | |
| 5,733,856 A | 3/1998 | Gopalkrishnan et al. | |
| 5,789,369 A | 8/1998 | Gopalkrishnan et al. | |
| 6,159,916 A | 12/2000 | Robbins et al. | |
| 6,187,738 B1 | 2/2001 | Micciche et al. | |
| 6,221,823 B1 | 4/2001 | Crisani et al. | |
| 6,242,402 B1 | 6/2001 | Robbins et al. | |
| 6,315,835 B1 | 11/2001 | Kerobo et al. | |
| 6,420,329 B1 | 7/2002 | Callaghan et al. | |
| 6,455,486 B1 | 9/2002 | Kerobo et al. | |
| 6,559,112 B2 | 5/2003 | Fox et al. | |
| 6,627,590 B1 | 9/2003 | Sherry et al. | |
| 6,897,188 B2 | 5/2005 | Gohl et al. | |
| 7,189,685 B2 | 3/2007 | Hubig et al. | |
| 2005/0170991 A1 * | 8/2005 | Ruland et al. | ............... 510/421 |
| 2005/0181967 A1 | 8/2005 | Ruland et al. | |

FOREIGN PATENT DOCUMENTS

| | | |
|---|---|---|
| EP | 0669906 | 5/1997 |
| EP | 0669907 | 5/1997 |
| JP | 2003336092 | 11/2003 |
| JP | 2004035755 | 2/2004 |
| JP | 2004091686 | 3/2004 |
| WO | WO 03/091190 | * 11/2003 |

OTHER PUBLICATIONS

U.S. Appl. No. 11/932,420, Dailey, filed Oct. 31, 2007, 117 pages.
English language translation and abstract for JP 2004091686 extracted from Japanese Patent Office, 31 pages, Mar. 25, 2003.
English language translation and abstract for JP 2004035755 extracted from Japanese Patent Office, 16 pages, Feb. 5, 2004.
English language translation and abstract for JP 2003336092 extracted from Japanese Patent Office, 14 pages, Nov. 28, 2003.
English language abstract for JP 2004091686 extracted from Japanese Patent Office, 28 pages, Mar. 25, 2004.
English language translation of European Patent Application No. EP 0611269.5, filed Feb. 22, 2006, 37 pages.

* cited by examiner

Primary Examiner—Brian P Mruk

(57) ABSTRACT

A surfactant composition includes a first surfactant, a second surfactant, and a polyalkylene glycol. The first surfactant is of the general formula $R^1$—O—$(A)_m$H, wherein $R^1$ is an aliphatic hydrocarbon having 10 carbon atoms, A is an alkyleneoxy group having from 2 to 5 carbon atoms, and m is a positive number. The second surfactant is of the general formula $R^2$—O—$(B)_n$H, wherein $R^2$ is an aliphatic hydrocarbon having from 12 to 14 carbon atoms, B is an alkyleneoxy group having from 2 to 5 carbon atoms, and n is a positive number. The polyalkylene glycol is present in the surfactant composition in an amount of from 3 to 20 parts by weight per 100 parts by weight of the surfactant composition.

42 Claims, No Drawings

SURFACTANT COMPOSITION AND METHOD OF FORMING

RELATED APPLICATIONS

This application claims priority to and all the advantages of European Patent Application No. EP 06110269.5, filed on Feb. 22, 2006.

FIELD OF THE INVENTION

The present invention generally relates to a surfactant composition. More specifically, the present invention relates to a surfactant composition including a first surfactant having from 8 to 11 carbon atoms, a second surfactant having from 12 to 14 carbon atoms, and a polyalkylene glycol.

DESCRIPTION OF THE RELATED ART

Surfactant compositions are well known in the art, especially those used in an industrial and institutional (I&I) cleaning formulation. The I&I cleaning formulation is used to remove dirt, oil, grease, and the like, from a surface in a variety of environments. Surfactant compositions used in I&I formulations typically increase wetting, i.e., contact of the I&I cleaning formulation with the surface, which facilitates removal of dirt, oil, and grease from the surface. However, many of these surfactant compositions include alkoxylated alkyl phenols, a chemical family that, together with their degradation products such as nonylphenol (NP), are potentially hazardous, non-biodegradable, and may be toxic to certain types of aquatic life. Many known surfactant compositions also display erratic foaming tendencies, do not resist gelling upon dilution with water, and have elevated critical micelle concentrations thereby requiring increased amounts of the surfactant compositions to be used in the I&I cleaning formulation, which increases costs of the I&I cleaning formulation. Many of these surfactant compositions also do not reduce surface tension of water under both static and dynamic conditions and thereby do not allow for optimum performance in both pour and spray applications. As a result, many of these known surfactant compositions have limited usefulness.

One particular surfactant composition, disclosed in Japanese Patent Publication Number 2004035755A, includes alkylene oxide adducts of aliphatic alcohols and also includes an organic diluent such an alkyl alcohol and/or a glycol, which is used to dilute the composition in amounts of from 5 to 95% by weight. Dilution of the surfactant composition in such varied amounts greatly decreases the efficacy of the surfactant composition in reducing surface tension of water, in controlling an amount of foaming, and in forming micelles at low concentrations. As a result, these varied amounts of dilution minimize any benefits to cleaning provided by this surfactant composition.

Although the known surfactant compositions, such as the composition of the '755 publication, are widely used, there remains an opportunity to form a biodegradable surfactant composition and reduce an amount of alkoxylated phenols used in I&I cleaning formulations. There also remains an opportunity to form a surfactant composition with improved physical properties, e.g., controlled levels of foaming, decreased gelling upon dilution with water, decreased critical micelle concentrations, and increased solubility in alkaline compositions. There further remains an opportunity to form a surfactant composition that reduces the surface tension of water under both static and dynamic conditions at low concentrations thereby optimizing performance in both low mechanical action applications and high mechanical (spray) applications. Still further, there remains an opportunity to form a surfactant composition that contributes to cleaning performance of I&I cleaning formulations.

SUMMARY OF THE INVENTION AND ADVANTAGES

The present invention provides a surfactant composition. The surfactant composition includes a first surfactant of the general formula $R^1$—O—$(A)_m$H, wherein $R^1$ is an aliphatic hydrocarbon having from 8 to 11 carbon atoms, A is an alkyleneoxy group having from 2 to 5 carbon atoms, and m is a positive number. The surfactant composition also includes a second surfactant of the general formula $R^2$—O—$(B)_n$H, wherein $R^2$ is an aliphatic hydrocarbon having from 12 to 14 carbon atoms, B is an alkyleneoxy group having from 2 to 5 carbon atoms, and n is a positive number. Further, the surfactant composition includes a polyalkylene glycol present in an amount of from 3 to 20 parts by weight per 100 parts by weight of the composition.

The present invention also provides a method of forming the surfactant composition. The method includes the step of alkoxylating a first aliphatic alcohol having from 8 to 11 carbon atoms in the presence of a catalyst to form the first surfactant and the polyalkylene glycol in situ. The method also includes the step of alkoxylating a second aliphatic alcohol having from 12 to 14 carbon atoms in the presence of the catalyst to form the second surfactant and the polyalkylene glycol in situ. Further, the method includes the step of combining the first surfactant, the second surfactant, and the polyalkylene glycol to form the surfactant composition.

The surfactant composition of the instant invention reduces the surface tension of water under both static and dynamic conditions at low concentrations thereby optimizing performance in both low mechanical action applications and high mechanical action (spray) applications by increasing surface wetting. The surfactant composition also resists gelling upon addition to water. When included in an industrial and institutional (I&I) cleaning formulation, the surfactant composition also contributes to cleaning performance due to solubility in alkaline compositions and a decreased critical micelle concentration such that a minimized amount of the surfactant composition can be used, thereby reducing costs.

DETAILED DESCRIPTION OF THE INVENTION

The instant invention provides a surfactant composition. The surfactant composition is preferably biodegradable. The terminology "biodegradable," as referenced herein, refers to a tendency of the surfactant composition to be chemically degraded via natural effectors such as soil bacteria, weather, plants and/or animals. The biodegradability of the surfactant composition reduces a possibility of pollution and formation of environmental hazards and is dependent on components of the surfactant composition.

The surfactant composition includes a first surfactant, a second surfactant, and a polyalkylene glycol. In one embodiment, the surfactant composition consists essentially of the first surfactant, second surfactant, and the polyalkylene glycol. In another embodiment, the surfactant composition consists of the first surfactant, the second surfactant, and the polyalkylene glycol.

The first surfactant is of the general formula $R^1-O-(A)_m$-H. In this formula, $R^1$ is an aliphatic hydrocarbon having from 8 to 11 carbon atoms. As is known in the art, aliphatic hydrocarbons may include straight, branched, and/or cyclic chains of carbon and hydrogen atoms which may be saturated or unsaturated. It is contemplated that $R^1$ may include a mixture of different aliphatic hydrocarbons having 8, 9, 10, and 11 carbon atoms. Alternatively, $R^1$ be an aliphatic hydrocarbon having 8 carbon atoms, 9 carbon atoms, 10 carbon atoms, or 11 carbon atoms. Preferably, $R^1$ is an aliphatic hydrocarbon having 10 carbon atoms. An example of a particularly suitable hydrocarbon having 10 carbon atoms includes, but is not limited to, a 2-propylheptane moiety. It is to be understood that the terminology "2-propylheptane moiety" refers to a $C_{10}H_{22}$ moiety bonded to the oxygen atom of the first surfactant. For descriptive purposes only, a chemical structure of the 2-propylheptane moiety is shown below:

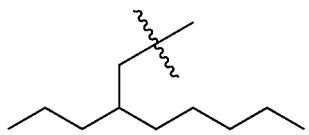

In another embodiment, the first surfactant is substantially free of aliphatic hydrocarbons having less than 8 carbon atoms and/or more than 11 carbon atoms. The terminology "substantially free" refers to an amount of the hydrocarbons of preferably of less than 10% by weight, more preferably of less than 5% by weight, and most preferably of less than 1% by weight, of the surfactant composition.

It is contemplated that the aliphatic hydrocarbon having from 8 to 11 carbon atoms may have any average degree of branching. That is, the aliphatic hydrocarbon having from 8 to 11 carbon atoms may have an average degree of branching of zero or may have an average degree of branching of greater than zero. Preferably, the aliphatic hydrocarbon having from 8 to 11 carbon atoms has an average degree of branching of approximately one. The degree of branching is defined as a number of carbon atoms in aliphatic hydrocarbon (3° carbon atoms) which are bonded to three additional carbon atoms, plus two times a number of carbon atoms (4° carbon atoms) which are bonded to four additional carbon atoms. The average degree of branching is calculated as a sum of all degrees of branching of individual aliphatic hydrocarbon molecules divided by a total number of the individual aliphatic hydrocarbon molecules. The degree of branching may be determined, for example, through use of $^{13}C$ NMR methods such as COSY, DEPT, INADEQUATE, followed by quantification via use of relaxation reagents. Other NMR methods and GC-MS methods may also be used.

In addition to $R^1$, A is an alkyleneoxy group having from 2 to 5 carbon atoms. The alkyleneoxy group may include, but is not limited to, ethyleneoxy groups (2 carbon atoms), propyleneoxy groups (3 carbon atoms), butyleneoxy groups (4 carbon atoms), pentoxy groups (5 carbon atoms), and combinations thereof. The butyleneoxy groups may include any or all of 1,2-butylene oxide groups, 2,3-butylene oxide groups, and isobutylene oxide groups. Most preferably, A is further defined as an ethyleneoxy group (2 carbon atoms).

Further, m is a positive number. As is known in the art, m represents a number of moles of the alkyleneoxy group added to the aliphatic hydrocarbon of the first surfactant. It is contemplated that m can be any whole number or any fraction greater than zero. In one embodiment, the first surfactant includes a mixture of molecules having differing numbers of moles of the alkyleneoxy group added to the aliphatic hydrocarbon molecules. Preferably, m is a number of from 3 to 50, more preferably of from 3 to 12, and most preferably of from 5 to 10. When m is greater than or equal to 2, it is contemplated that the alkyleneoxy groups may be distributed randomly or blockwise. Additionally, the first surfactant is preferably present in the surfactant composition in an amount of from 10 to 90, and more preferably of from 15 to 75, parts by weight per 100 parts by weight of the composition.

The first surfactant preferably has both an aqueous cloud point and a solvent cloud point of from 25 to 80, more preferably of from 30 to 70, and most preferably of from 40 to 70, ° C. As is known in the art, cloud point is a measure of a temperature where the (first) surfactant begins to phase separate such that two phases appear, thus making the (first) surfactant cloudy. To determine the aqueous cloud points, 1% by weight of the (first) surfactant is added to water and either heated to cooled. To determine the solvent cloud points, approximately 1 gram of the (first) surfactant is added to 99 grams of an aqueous solution including 25% by weight of butyldiglycol.

Further, the first surfactant preferably has a hydrophilic lipophilic balance (HLB) of from 7 to 15, more preferably of from 9 to 14, and most preferably of from 11 to 14, as determined by the Griffin method. As is known in the art, the HLB is a measure of the lipophilicity of the (first) surfactant based on an arbitrary scale of from 0 to 40, with higher values indicating a lower lipophilicity or greater hydrophilicity of the (first) surfactant.

Still further, the first surfactant preferably has a critical micelle concentration (CMC) at 25° C. of from 0.1 to 5, more preferably of from 0.1 to 2, and most preferably of from 0.1 to 1, g/L, as determined by a surface tension method well known in the art. The method includes production of a graph of surface tension vs log concentration of the (first) surfactant. The CMC is found as the point at which two lines intersect, i.e., the baseline of minimal surface tension and the slope where surface tension shows linear decline. To perform the method, a surface or interfacial tensiometer equipped with an automated dosimeter is utilized. A probe is chosen (e.g., a Wilhelmy plate or DuNouy ring) and a measuring vessel is filled with solute. The automated dosimeter is filled with concentrated (first) surfactant. A surface tension of the solute is measured prior to any addition of the (first) surfactant to the solute. Subsequently, an addition of the (first) surfactant is made to the solute and surface tension is measured. Additions of the (first) surfactant to the solute are then continuously made, and surface tensions measured, such that data is evenly spaced along a log scale of concentration. As is known in the art, CMC is a measure of the concentration of the (first) surfactant that represents a critical value above which increasing concentration of the (first) surfactant forces formation of micelles. A decreased CMC is indicative of an ability of the (first) surfactant to form micelles in solution at minimized concentrations leading to increased cleaning ability and decreased cost of use.

In addition to the first surfactant, the surfactant composition also includes the second surfactant. The second surfactant is of the general formula $R^2$—O—$(B)_n$H. In this formula, $R^2$ is an aliphatic hydrocarbon having from 12 to 14 carbon atoms. It is contemplated that $R^2$ may include a mixture of different aliphatic hydrocarbons having 10, 12, 14, and/or 16 carbon atoms. Alternatively, $R^2$ may be an aliphatic hydrocarbon having 12 carbon atoms or 14 carbon atoms. Preferably, $R^2$ is an aliphatic hydrocarbon having 12 carbon atoms. In one embodiment, the second surfactant includes approximately 55 percent by weight of molecules wherein $R^2$ is an aliphatic hydrocarbon having 12 carbon atoms and approximately 45 percent of molecules wherein $R^2$ is an aliphatic hydrocarbon having 14 carbon atoms. In one embodiment, the second surfactant includes only molecules having 12 carbon atoms. An example of a particularly suitable hydrocarbon having 12 carbon atoms includes, but is not limited to, a dodecane moiety. It is to be understood that the terminology "dodecane moiety" refers to a $C_{12}H_{25}$ moiety bonded to the oxygen atom of the second surfactant. Preferably, the oxygen atom is bonded to a primary carbon atom of the dodecane moiety, i.e., in a 1-dodecanol structure. In another embodiment, the second surfactant is substantially free of aliphatic hydrocarbons having less than 12 carbon atoms and/or more than 14 carbon atoms. The terminology "substantially free" refers to an amount of hydrocarbons preferably of less than 10% by weight, more preferably of less than 5% by weight, and most preferably of less than 1% by weight, of the surfactant composition.

Additionally, B is an alkyleneoxy group having from 2 to 5 carbon atoms and may be the same or may be different than A, first introduced above. Most preferably, B is an ethyleneoxy group (2 carbon atoms). Additionally, n is a positive number, may be any fraction or whole number greater than zero, and may be the same or different than m. In one embodiment, the second surfactant includes a mixture of molecules having differing numbers of moles of the alkyleneoxy group added to the aliphatic hydrocarbon molecules. Preferably, n is a number of from 3 to 50, more preferably of from 3 to 12, and most preferably of from 5 to 10. When n is greater than or equal to 2, it is contemplated that the alkyleneoxy groups may be distributed randomly or blockwise. Additionally, the second surfactant is preferably present in the surfactant composition in an amount of from 10 to 90, and more preferably of from 15 to 75, parts by weight per 100 parts by weight of the surfactant composition.

The second surfactant preferably has both an aqueous cloud point and a solvent cloud point of from 25 to 80, more preferably of from 30 to 70, and most preferably of from 40 to 70, ° C. Further, the second surfactant preferably has a hydrophilic lipophilic balance (HLB) of from 7 to 15, more preferably of from 9 to 14, and most preferably of from 11 to 14, as determined by the Griffin method. Still further, the second surfactant preferably has a CMC at 25° C. of from 0.0001 to 0.6, more preferably of from 0.002 to 0.3, and most preferably of from 0.002 to 0.06, g/L, as determined by a method well known in the art and described above.

In addition to the first and second surfactants, the surfactant composition also includes a polyalkylene glycol. The polyalkylene glycol may be specifically added to the surfactant composition or may be formed in situ while forming the first and or second surfactants, as described in greater detail below. The polyalkylene glycol preferably includes, but is not limited to, polyethylene glycol (PEG), polypropylene glycol (PPG), polybutylene glycol (PBG), and combinations thereof. Most preferably, the polyalkylene glycol is further defined as polyethylene glycol. The polyalkylene glycol may have any number average molecular weight up to approximately 12,000 g/mol. Preferably, the polyalkylene glycol has a number average molecular weight of from 200 to 12,000, more preferably of from 300 to 1,000, even more preferably of from 400 to 800, and most preferably of approximately 700, g/mol. For descriptive purposes only, a chemical structure of polyethylene glycol having a number average weight of approximately 700 g/mol is shown below:

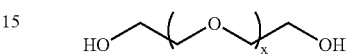

wherein x is an integer of approximately 22-24.

The polyalkylene glycol is present in an amount of from 3 to 20 parts by weight per 100 parts by weight of the surfactant composition. More preferably, the polyalkylene glycol is present in an amount of from 5 to 15, and most preferably of from 8 to 10, parts by weight per 100 parts by weight of the surfactant composition. In one embodiment, the surfactant composition includes from 18 to 19 parts by weight of the first surfactant, from 72 to 73 parts by weight of the second surfactant, and approximately 8 to 10 parts by weight of the polyalkylene glycol, per 100 parts by weight of the surfactant composition. In another embodiment, the surfactant composition includes from 72 to 73 parts by weight of the first surfactant, from 18 to 19 parts by weight of the second surfactant, and approximately 8 to 10 parts by weight of the polyalkylene glycol, per 100 parts by weight of the surfactant composition.

In addition to the first surfactant, the second surfactant, and the polyalkylene glycol, the surfactant composition may also include, but does not require, an additional surfactant that is different from the first and second surfactants. If the additional surfactant is included in the surfactant composition, it may only be included in addition to both the first and second surfactants. The additional surfactant may include, but is not limited to, aliphatic and/or aromatic alkoxylated alcohols, LAS (linear alkyl benzene sulfonates), paraffin sulfonates, FAS (fatty alcohol sulfates), FAES (fatty alcohol ethersulfates), and combinations thereof. Examples of suitable non-limiting additional surfactants include methylethylene glycols, butylethylene glycols, pentylethylene glycols, hexylethylene glycols, butylpropylene glycols, trimethylolpropane ethoxylates, glycerol ethoxylates, pentaerythritol ethoxylates, alkoxylates of bisphenol A, and alkoxylates of 4-methylhexanol and 5-methyl-2-propylheptanol.

Once formed, the surfactant composition preferably has both an aqueous cloud point and a solvent cloud point of from 25 to 80, more preferably of from 30 to 70, and most preferably of from 40 to 70, ° C. The surfactant composition can be a liquid, a solid, or a gel paste. The surfactant composition preferably has a pH of from 5 to 8 and more preferably of from 6 to 7. The surfactant composition also preferably has an Average Percent Cleaning, of from 40 to 100, more preferably of from 60 to 100, still more preferably of from 70 to 100, and most preferably of from 80 to 100, percent, as determined in both scrub and spray tests. The Average Percent Cleaning in both scrub and spray tests is determined by the methods described in greater detail in the Examples below. The surfactant composition also preferably forms a contact angle with lime soap soil of from 30 to 90, more preferably of from 40 to 80, and most preferably of from 45 to 75, degrees, measured with a contact angle goniometer at a time of from 0.1 to 10 seconds. The lime soap soil used to determine contact angle is formed according to Chemical Specialty Products Association (CSPA) method DCC-16. To measure contact angle, the surfactant composition is present in an aqueous solution at a concentration of approximately 500 parts per million. The contact angle is determined by the method described in greater detail in the Examples below. Further, the surfactant composition preferably has a Draves Wetting value of less than 80, more preferably of less than 30, and most preferably of less than 20, seconds.

The instant invention also provides a method of forming the surfactant composition. The method includes the step of alkoxylating a first aliphatic alcohol having from 8 to 11 carbon atoms in the presence of a catalyst to form the first surfactant and the polyalkylene glycol in situ. Preferably, the catalyst is a metal catalyst, e.g., sodium hydroxide, which is described in greater detail below. As is known in the art, the terminology "in situ", relative to the step of alkoxylating the first aliphatic alcohol, refers to formation of the polyalkylene glycol in an original place, i.e., in the same reaction vessel as is used to form the first surfactant, and by the same reaction used to form the first surfactant.

The step of alkoxylating the first aliphatic alcohol preferably includes reacting a metal catalyst, i.e., a metal hydroxide catalyst, with the first aliphatic alcohol to form an alkoxide ($M^+O^-$). This step may be completed in the presence or absence of water. After the alkoxide is formed, the alkoxide is preferably reacted with an alkylene oxide to form the first surfactant and form the polyalkylene glycol in situ. For descriptive purposes only, a chemical reaction scheme of the alkoxylation of the first aliphatic alcohol to form the first surfactant and the polyalkyleneglycol is generically shown below:

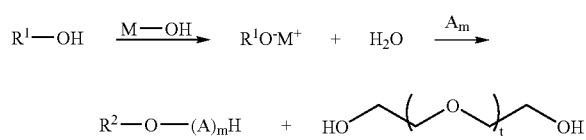

wherein t is a positive number.

The first aliphatic alcohol may include any aliphatic alcohol having from 8 to 11 carbon atoms. In one embodiment the first aliphatic alcohol includes a mixture of different aliphatic alcohols having 8, 9, 10, and/or 11 carbon atoms. Alternatively, the first aliphatic alcohol may have 8 carbon atoms, 9 carbon atoms, 10 carbon atoms, or 11 carbon atoms. Preferably, the first aliphatic alcohol has 10 carbon atoms and includes 2-propylheptanol. For descriptive purposes only, a chemical structure of 2-propylheptanol is shown below:

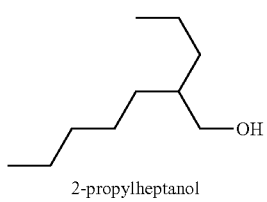

2-propylheptanol

The metal catalyst preferably includes an alkali metal or alkaline earth metal hydroxide, but may include any metal catalyst known in the art including transition metal organometallic catalysts. Particularly suitable alkali metal catalysts include, but are not limited to, sodium hydroxide, potassium hydroxide, rubidium hydroxide, cesium hydroxide, and combinations thereof. The metal catalyst may be a single metal catalyst or may include a mixture of metal catalysts, as determined by one of skill in the art.

In addition to the step of alkoxylating the first aliphatic alcohol, the method also includes the step of alkoxylating a second aliphatic alcohol having from 12 to 14 carbon atoms in the presence of the metal catalyst to form the second surfactant and the polyalkylene glycol in situ. As first described above, the terminology "in situ", relative to the step of alkoxylating the second aliphatic alcohol, refers to formation of the polyalkylene glycol in the original place, i.e., in the same reaction vessel as is used to form the second surfactant, and by the same reaction used to form the second surfactant.

The step of alkoxylating the second aliphatic alcohol includes reacting the catalyst with the second aliphatic alcohol to form an alkoxide. This step may also be completed in the presence or absence of water. After the alkoxide is formed, the alkoxide is reacted with an alkylene oxide to form the second surfactant and form the polyalkylene glycol in situ. For descriptive purposes only, a chemical reaction scheme of the alkoxylation of the second aliphatic alcohol to form the second surfactant and the polyalkyleneglycol is generically shown below:

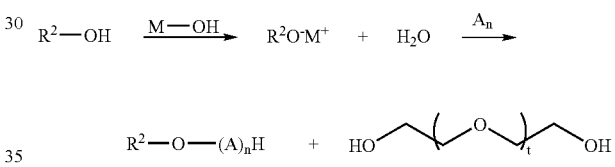

wherein t is a positive number.

The second aliphatic alcohol may include any aliphatic alcohol having from 12 to 14 carbon atoms. Preferably, the second aliphatic alcohol includes a mixture of different alcohols having 12, 13, and 14 carbon atoms. Preferably, the second aliphatic alcohol includes a mixture of 1-dodecanol and 1-tetradecanol in a ratio of from 5:95 to 95:5. More preferably, the second aliphatic alcohol includes a mixture of 1-dodecanol and 1-tetradecanol in a ratio of 55:45.

It is contemplated that the step of alkoxylating the first aliphatic alcohol may be completed separately from, or simultaneously with, the step of alkoxylating the second aliphatic alcohol. Also, the first and second aliphatic alcohols may be alkoxylated in the same vessel or in different vessels. Preferably, the first and second aliphatic alcohols are alkoxylated simultaneously in the same vessel. It is contemplated that if the first and second alcohols are alkoxylated simultaneously in the same vessel, then the polyalkylene glycol formed in situ may be formed from one or both of the reactions to form the first surfactant and/or the second surfactant.

The steps of alkoxylating the first and second aliphatic alcohols may be completed at any temperature and at any pressure. Preferably, these steps are completed at a temperature of from 100° C. to 160° C. and at a pressure of from 20 psig to 100 psig. For descriptive purposes only, a preferred chemical reaction scheme including the ethoxylation of the first and second aliphatic alcohols in the presence of potassium hydroxide as the metal catalyst, to form the polyethylene glycol in situ, is shown below:

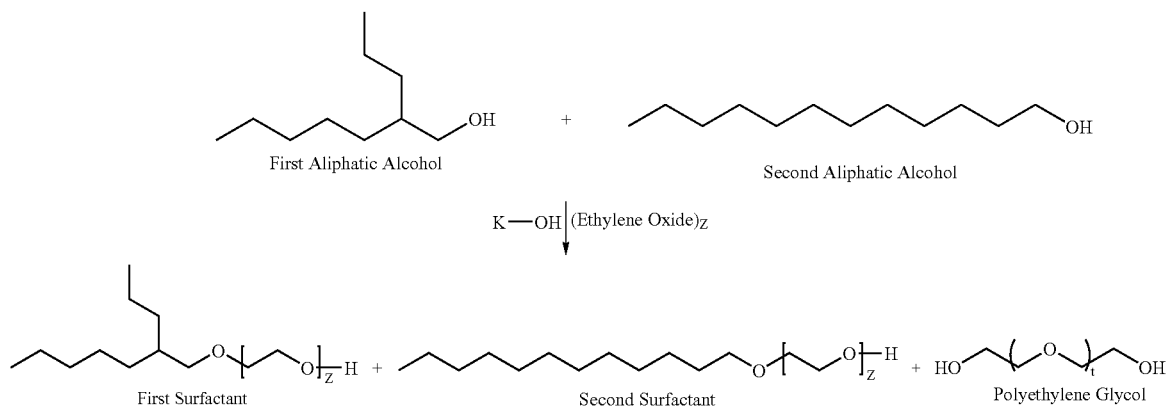

wherein z is a number of from 5 to 12 and t is a number of from 22-24.

The surfactant composition of the instant invention has a variety of uses and can be included as a component in various industrial formulations. The surfactant composition may be included in one or more of these industrial formulations in varying amounts. Preferably, the surfactant composition is included in the industrial formulations in an amount of from 0.5 to 20, and more preferably of from 2 to 10, parts by weight per 100 parts by weight. Examples of suitable industrial formulations include, but are not limited to, those used in cleaning, coating, degreasing, leveling, painting, finishing and electroplating, lubricating, humectants, cosmetics, pharmaceuticals, crop protection, dyes and pigments, adhesives, food preparation, water treatment, fermentation, mineral processing, building auxiliaries, emulsions and dispersions, coolants, and combinations thereof. Additional non-limiting examples of suitable industrial formulations include cleaning in place solutions, general cleansers and sanitizers, chain lubricants, warewashing formulations, laundry formulations, vehicle washing formulations, emulsion polymerization formulations, de-inking and pulp dissolving formulations, and combinations thereof.

One particularly suitable industrial formulation is an industrial and institutional (I&I) cleaning formulation. When included in I&I cleaning formulations, the surfactant composition reduces the surface tension of water under both static and dynamic conditions at low concentrations thereby optimizing performance in both scrubbing and spray applications by increasing surface wetting. The surfactant composition also resists gelling upon addition to water, has a decreased point of aqua toxicity, and has a decreased critical micelle concentration such that a minimized amount of the surfactant composition can be used in the I&I cleaning formulations, thereby reducing costs. The surfactant composition also contributes to removal of stains and residues, such as rust, lime soap, and metal salts of fatty acids, in addition to oily, particulate, oxidizable, and enzyme stains, from both hard and soft surfaces. Non-limiting examples of hard surfaces are those found in kitchens and bathrooms, on walls and floors, in showers and bathtubs, on countertops and cabinets, on vehicles, and on marble, glass, metal, vinyl, fiberglass, ceramic, granite, concrete, acrylic, Formica®, Silestone®, Corian®, and laminated surfaces. Examples of soft surfaces include, but are not limited to, fabrics, textiles, and carpets. It is also contemplated that the I&I cleaning formulations may be applied in outdoor environments on exterior surfaces such as on driveways, patios, siding, decking, and the like.

The I&I cleaning formulation may include the surfactant composition in addition, but not limited, to water, builders, bleaches, enzymes, solvents, salts, graying inhibitors, soil release polymers, color transfer inhibitors, foam inhibitors, complexing agents, optical brighteners, fragrances, fillers, inorganic extenders, formulation auxiliaries, solubility improvers, opacifiers, dyes, corrosion inhibitors, peroxide stabilizers, electrolytes, water, soaps, detergents, acids such as phosphoric acid, amidosulfonic acid, citric acid, lactic acid, acetic acid, peracids, and trichloroisocyanuric acid, solvents such as ethylene glycol, 2-butoxyethanol, butyldiglycol, alkyl glycol ethers, and isopropanol, chelating agents such as EDTA, NTA (N,N,N-nitrilotriacetic acid), and MGDA (2-methylglycine-N,N-diacetic acid), phosphonates, polymers, such as polyacrylates, copolymers of maleic acid and acrylic acid, alkali donors such as hydroxides, silicates, carbonates, phosphates, perfumes, oils, oxidizing agents such as perborates, dichloroisocyanurates, enzymes, interface-active ethyleneoxy adducts, and combinations thereof. Although the I&I cleaning formulation may include any amount of water, as determined by one of skill in the art, the water is preferably included in an amount of from 5 to 95% by weight, more preferably of from 10 to 90% by weight, still more preferably of from 50 to 90% by weight, and most preferably of from 70 to 90% by weight, of the I&I cleaning formulation.

Particularly suitable builders include both inorganic and organic builders. Preferably, the inorganic builders include crystalline and/or amorphous alumosilicates with ion-exchanging properties, such as zeolites. Various types of zeolites may be used including, but not limited to, A, X, B, P, MAP and HS zeolites in sodium form or in forms in which sodium is partially exchanged for lithium, potassium, calcium, magnesium, and/or ammonium. In one embodiment, the inorganic builders include carbonates and hydrogencarbonates as alkali metal salts, alkaline earth metal salts, and/or ammonium salts. Alternatively, the inorganic builder may include polyphosphates such as pentasodium triphosphate. One or more inorganic builders may be present in the I&I cleaning formulation in any amount or any ratio. Preferably, the inorganic builder includes a mixture of alumosilicates and carbonates in a weight ratio of 98:2 to 20:80 and more preferably of 85:15 to 40:60. Alternatively, the inorganic builder may be present in the I&I cleaning formulation in an amount of from 5 to 50% by weight.

The organic builders preferably include di-silicates and/or sheet silicates that may include alkali metal silicates, alkaline earth metal silicates, and/or ammonium silicates. Amorphous silicates such as sodium metasilicate may also be used. In one embodiment, the organic builder includes an acid selected from the group of carboxylic acids, copolymers of carboxylic acids, terpolymers of carboxylic acids, graft polymers of carboxylic acids, polyglyoxylic acids, polyamidocarboxylic acids, phosphonic acids, and combinations thereof.

Particularly suitable carboxylic acids include $C_4$-$C_{20}$ di-, tri- and tetra-carboxylic acids such as succinic acid, propanetricarboxylic acid, butanetetracarboxylic acid, and cyclopentanetetracarboxylic acid, $C_4$-$C_{20}$ hydroxycarboxylic acids such as malic acid, tartaric acid, gluconic acid, glutaric acid, citric acid, and lactobionic acid, sucrose mono-, di- and tricarboxylic acids, alkyl- and alkenyl-succinic acids having $C_2$-$C_{16}$ alkyl and/or alkenyl radicals, aminopolycarboxylic acids such as nitrilotriacetic acid, 3-alaninediacetic acid, ethylenediaminetetraacetic acid, serinediacetic acid, isoserinediacetic acid, methylglycinediacetic acid and alkylethylenediamine triacetates, oligomaleic acids, co- and terpolymers of unsaturated $C_4$-$C_8$ dicarboxylic acids such as maleic acid, fumaric acid, itaconic acid and citraconic acid, monoethylenically unsaturated $C_3$-$C_8$ monocarboxylic acids such as acrylic acid, methacrylic acid, crotonic acid and vinylacetic acid, and combinations thereof.

Examples of suitable copolymers of dicarboxylic acids include, but are not limited to, copolymers of maleic acid and acrylic acid in a weight ratio of 100:90 to 95:5 and more preferably of 30:70 to 90:10 with molar masses from 100,000 to 150,000, and copolymers of maleic acid with $C_2$-$C_8$ olefins in a molar ratio 40:60 to 80:20. A non-limiting example of a suitable terpolymer of the carboxylic acids includes a terpolymer of maleic acid, acrylic acid and a vinyl ester of a $C_1$-$C_3$ carboxylic acid in a weight ratio of 10 (maleic acid):90 (acrylic acid+vinyl ester): 95 (maleic acid):10 (acrylic acid+vinyl ester), where the weight ratio of acrylic acid to the vinyl ester can be from 30:70 to 70:30.

Suitable examples of graft polymers of carboxylic acids include a graft base and an unsaturated carboxylic acid. The carboxylic acid may include, but is not limited to, maleic acid, fumaric acid, itaconic acid, citraconic acid, acrylic acid, methacrylic acid, crotonic acid vinylacetic acid, and combinations thereof. Suitable graft bases included in the graft polymers of the carboxylic acids include degraded polysaccharides such as acidically and/or enzymatically degraded starches, inulins, cellulose, protein hydrolysates, reduced degraded polysaccharides such as mannitol, sorbitol, aminosorbitol and N-alkylglucamine, alkylene oxide block copolymers such as ethylene oxide/propylene oxide block copolymers, ethylene oxide/butylene oxide block copolymers, ethylene oxide/propylene oxide/butylene oxide block copolymers, and alkoxylated mono- or polyhydric $C_1$-$C_7$ alcohols and/or $C_{15}$-$C_{22}$ alcohols that are different from the first and second surfactants. It is to be understood that if alkoxylated mono- or polyhydric $C_1$-$C_7$ alcohols and/or $C_{15}$-$C_{22}$ alcohols are included in the I&I cleaning formulation, these alkoxylated alcohols are not equivalent to the first and second surfactants and may only be included in addition to the first and second surfactants. In one embodiment, 20 to 80 parts by weight of the carboxylic acid per 100 parts by weight of the graft base, may be polymerized. In this embodiment, a mixture of maleic acid and acrylic acid in the weight ratio from 90:10 to 10:90 is preferably polymerized with the graft base.

Additionally, the organic builder may include a polyaspartic acid or a co-condensate of aspartic acid with one or more amino acids including, but not limited to, $C_4$-$C_{25}$ mono- or di-carboxylic acids and/or $C_4$-$C_{25}$ mono- or di-amines. In one embodiment, the co-condensate includes a polyaspartic acid modified with $C_6$-$C_{22}$ mono- or di-carboxylic acids or with $C_6$-$C_{22}$ mono- or di-amines in acids including phosphorous.

Further, the organic builder may include a condensation product of citric acid and a hydroxycarboxylic acid or a polyhydroxy compound. Most preferably, the condensation products of citric acid include carboxyl groups and have number average molecular weights of up to 10,000 g/mol. Still further, the organic builder may include ethylenediaminedisuccinic acid, oxydisuccinic acid, aminopolycarboxylates, aminopolyalkylene phosphonates, polyglutamates, and combinations thereof. Also, a non-limiting example of a suitable phosphonic acid includes hydroxyethanediphosphonic acid.

Alternatively, the organic builder may be selected from the group of olefins, ethers, esters, amines, oxidized starches, and combinations thereof. Suitable olefins, ethers, esters, and amines include, but are not limited to, monoethylenically unsaturated $C_2$-$C_{22}$ olefins, vinyl alkyl ethers with $C_1$-$C_8$ alkyl groups, styrene, vinyl esters of $C_1$-$C_8$ carboxylic acids, (meth)acrylamide and vinylpyrrolidone, (meth)acrylic esters of $C_1$-$C_8$ alcohols, (meth)acrylonitrile, (meth)acrylamides of $C_1$-$C_8$ amines, N-vinylformamide and vinylimidazole. In one embodiment, the organic builder is present in the I&I cleaning formulation in an amount of from 0.1 to 20% by weight.

In addition to, and different from the first and second surfactants and any additional surfactants included in the surfactant composition, the I&I cleaning formulation may include additional surfactants including non-ionic, cationic, anionic, and/or ampholytic surfactants. Suitable anionic surfactants include, but are not limited to, fatty alcohol sulfates of fatty alcohols having from 8 to 22, and more preferably from 10 to 18, carbon atoms, e.g., $C_9$-$C_{11}$ alcohol sulfates, $C_{12}$-$C_{14}$ alcohol sulfates, cetyl sulfate, myristyl sulfate, palmityl sulfate, stearyl sulfate, tallow fatty alcohol sulfate, and combinations thereof. Further non-limiting examples of suitable anionic surfactants include alkanesulfonates, such as $C_8$-$C_{24}$ alkylsulfonates, soaps such as alkali metal salts of $C_8$-$C_{24}$ carboxylic acids, $C_9$-$C_{20}$ linear alkylbenzenesulfonates, and $C_9$-$C_{20}$ linear alkyltoluenesulfonates. Still further, the anionic surfactant may include $C_8$-$C_{24}$ olefinsulfonates and di-sulfonates, mixtures of alkene- and hydroxyalkane-sulfonates or di-sulfonates, alkyl ester sulfonates, sulfonated polycarboxylic acids, alkyl glyceryl sulfonates, fatty acid glycerol ester sulfonates, alkylphenol polyglycol ether sulfates, paraffinsulfonates having from 20 to 50 carbon atoms, alkyl phosphates, acyl isothionates, acyl taurates, acyl methyl taurates, alkylsuccinic acids, alkenylsuccinic acids and corresponding esters and amides thereof, alkylsulfosuccinic acids and corresponding amides, mono- and di-esters of sulfosuccinic acids, acyl sarcosinates, sulfated alkyl polyglucosides, alkyl polyglycol carboxylates, hydroxyalkyl sarcosinates, and combinations thereof. The anionic surfactant may be a salt such as an alkali metal salt and/or an ammonium salt such as a hydroxyethylammonium, di(hydroxyethyl)ammonium, and/or tri(hydroxyethyl)ammonium salt. In one embodiment, the anionic surfactant is present in the I&I cleaning formulation in an amount of from 3 to 30% by weight.

Suitable non-ionic surfactants include, but are not limited to, alkylphenol alkoxylates, alkyl polyglucosides, hydroxyalkyl polyglucosides, N-alkylglucamides, alkylene oxide block copolymers, polyhydroxy and polyalkoxy fatty acid derivatives, and combinations thereof. The alkylphenol alkoxylates may include alkylphenol ethoxylates having $C_6$-$C_{14}$ alkyl chains and from 5 to 30 moles of alkylene oxide added to the alkyl chains. The alkyl polyglucosides and/or hydroxyalkyl polyglucosides may have from 8 to 22 carbon atoms in an alkyl chain and have from 1 to 20 glucoside units. The N-alkylglucamides may have $C_6$-$C_{22}$ alkyl chains and may be formed from acylation of reductively aminated sugars with corresponding long-chain carboxylic acid derivatives. Further, the alkylene oxide block copolymers may include block copolymers of ethylene oxide, propylene oxide and/or butylene oxide. Still further, the polyhydroxy and/or polyalkoxy fatty acid derivatives may include polyhydroxy fatty acid amides, N-alkoxy- and/or N-aryloxy-polyhydroxy fatty acid amides, fatty acid amide ethoxylates, and also fatty acid alkanolamide alkoxylates. In one embodiment, the non-ionic surfactant is present in the I&I cleaning formulation in an amount of from 1 to 20% by weight. In another embodiment, the additional surfactants include a mixture of anionic and non-ionic surfactants in a weight ratio from 95:5 to 20:80 and more preferably from 80:20 to 50:50.

In addition to the anionic and/or non-ionic surfactants, the additional surfactant may alternatively include cationic surfactants. Suitable cationic surfactants include, but are not limited to, interface-active compounds including ammonium groups such as alkyldimethylammonium halides and compounds having the chemical formula RR'R"R'"$N^+X^-$ wherein R, R', R", and R'" are independently selected from the group of alkyl groups, aryl groups, alkylalkoxy groups, arylalkoxy groups, hydroxyalkyl(alkoxy) groups, and hydroxyaryl (alkoxy) groups and wherein X is an anion. In one embodiment, the cationic surfactant is present in the I&I cleaning formulation in an amount of from 0.1 to 25 percent by weight.

Further, the additional surfactant may include ampholytic surfactants. Suitable ampholytic surfactants include, but are not limited to, aliphatic derivatives of secondary and/or tertiary amines which include an anionic group, alkyldimethylamine oxides, alkyl- and/or alkoxymethylamine oxides, and combinations thereof. In one embodiment, the ampholytic surfactant is present in the I&I cleaning formulation in an amount of from 0.1 to 25 percent by weight of the I&I cleaning formulation.

The I&I cleaning formulation may also include a bleach, as first introduced above. The bleach may include, but is not limited to, alkali metal perborates, alkali metal carbonate perhydrates, peracids, and combinations thereof. Suitable examples of peracids include, but are not limited to, peracetic acid, $C_1$-$C_{12}$ percarboxylic acids, $C_8$-$C_{16}$ dipercarboxylic acids, imidopercaproic acids, aryldipercaproic acids, linear and branched octane-, nonane-, decane- or dodecane-monoperacids, decane- and dodecane-diperacid, mono- and di-perphthalic acids, isophthalic acids and terephthalic acids, phthalimidopercaproic acid, terephthaloyldipercaproic acid, polymeric peracids, salts thereof, and combinations thereof. The bleach may be present in the I&I cleaning formulation in an amount of from 0.5 to 30% by weight.

The I&I cleaning formulation may also include a bleach activator present in an amount of from 0.1 to 15% by weight. The bleach activator may include, but is not limited to, polyacylated sugars, e.g., pentaacetylglucose, acyloxybenzenesulfonic acids and alkali metal and alkaline earth metal salts thereof, e.g., sodium p-isononanoyloxybenzenesulfonate and sodium p-benzoyloxybenzenesulfonate, N,N-diacetylated and N,N,N',N'-tetraacylated amines, e.g., N,N,N',N'-tetraacetylmethylenediamine and -ethylenediamine (TAED), N,Ndiacetylaniline, N,N-diacetyl-p-toluidine or 1,3-diacylated hydantoins, such as 1,3-diacetyl-5,5-dimethylhydantoin, N-alkyl-N-sulfonylcarboxamides, e.g., N-methyl-N-mesylacetamide and N-methyl-N-mesylbenzamide, N-acylated cyclic hydrazides, acylated triazoles and urazoles, e.g., monoacetylmaleic acid hydrazide, O,N,N-trisubstituted hydroxylamines, e.g., O-benzoyl-N,N-succinylhydroxylamine, O-acetyl-N,N-succinylhydroxylamine and O, N,N-triacetylhydroxylamine, N,N'-diacylsulfurylamides, e.g., N,N'-dimethyl-N,N'-diacetylsulfurylamide and N,N'-diethyl-N,N'-dipropionylsulfurylamide, triacyl cyanurates, e.g., triacetyl cyanurate and tribenzoyl cyanurate, carboxylic anhydrides, e.g., benzoic acid anhydride, m-chlorobenzoic anhydride and phthalic anhydride, 1,3-diacyl-4,5-diacyloxyimidazolines, e.g., 1,3-diacetyl-4,5-diacetoxyimidazoline, tetraacetylglycoluril, tetrapropionylglycoluril, diacylated 2,5-diketopiperazines, e.g., 1,4-diacetyl-2,5-diketopiperazine, acylation products of propylenediurea and 2,2-dimethylpropylenediurea, e.g., tetraacetylpropylenediurea, a-acyloxypolyacylmalonamides, e.g., a-acetoxy-N,N'-diacetylmalonamide, diacyldioxohexahydro-1,3,5-triazines, e.g., 1,5-diacetyl-2,4-dioxohexahydro-1,3,5-triazine, benz (4H)-1,3-oxazin-4-ones with alkyl radicals, e.g., methyl, or aromatic radicals, and combinations thereof.

The bleach may also be combined with a bleach catalyst. The bleach catalyst may include, but is not limited to, quaternized imines, sulfonimines, manganese complexes, and combinations thereof. The bleach catalyst may be included in the I&I cleaning formulation in amounts up to 1.5% by weight.

The I&I cleaning formulations may also include an enzyme, as introduced above. The enzyme may include, but is not limited to, proteases such as Savinase® and Esperase®, lipases such as Lipolase®, cellulases such as Celluzym, and combinations thereof. Each of the Savinase®, Esperase®, Lipolase®, and Celluzym are commercially available from Novo Nordisk of Princeton, N.J. In one embodiment, the I&I cleaning formulation includes an enzyme present in an amount of from 0.1 to 4% by weight.

Suitable graying inhibitors include, but are not limited to, polyesters of polyethylene oxides with ethylene glycol and/or propylene glycol and aromatic dicarboxylic acids or aromatic and aliphatic dicarboxylic acids, polyesters of polyethylene oxides terminally capped at one end with di- and/or polyhydric alcohols or dicarboxylic acids, and combinations thereof. Suitable soil release polymers include, but are not limited to, amphiphilic graft polymers or copolymers of vinyl esters and/or acrylic esters onto polyalkylene oxides or modified celluloses, such as methylcellulose, hydroxypropylcellulose, and carboxymethylcellulose, and combinations thereof. In one embodiment, the I&I cleaning formulation includes the soil release polymer present in an amount of from 0.3 to 1.5% by weight. Suitable color transfer inhibitors include, but are not limited to, color transfer inhibitors, for example homopolymers and copolymers of vinylpyrrolidone, of vinylimidazole, of vinyloxazolidone and of 4-vinylpyridine N-oxide having number average molecular weights of from 15,000 to 100,000 g/mol. In one embodiment, the I&I cleaning formulation includes the color transfer inhibitor present in an amount of from 0.05 to 5% by weight. Suitable foam inhibitors include, but are not limited to, organopolysiloxanes, silica, paraffins, waxes, microcrystalline waxes, and combinations thereof.

EXAMPLES

A series of surfactant compositions (Compositions 1-21) are formed according to the present invention. Specifically, amounts of the First Aliphatic Alcohol and the Second Aliphatic Alcohol are added to a vessel and mixed. Subsequently, potassium hydroxide (KOH) as the Metal Catalyst is added to the vessel and mixed with the First Aliphatic Alcohol and the Second Aliphatic Alcohol to form a mixture. The mixture is heated to 85° C. and agitated for 1 hour. Subsequently, the mixture is heated to 110° C. and adjusted to a pressure of approximately 90 psig. Then, Ethylene Oxide is added to the mixture to react with the First Aliphatic Alcohol and the Second Aliphatic Alcohol, thereby forming the First Surfactant and the Second Surfactant, forming the Polyethylene Glycol in situ, and forming the Compositions 1-21. The Ethylene Oxide is added to the mixture at a rate of approximately 1100-1200 gm/hr while the temperature of the mixture is allowed to increase to approximately 145° C. After formation of the First Surfactant, Second Surfactant, and Polyethylene Glycol, the temperature of the reaction vessel is lowered to approximately 80° C.

Amounts of each of the Metal Catalyst, the First Alcohol, the Second Alcohol, and the Ethylene Oxide, used to form the Compositions, are set forth in Table 1 below, wherein all amounts are in grams unless otherwise indicated.

TABLE 1

| Components | Composition 1 | Composition 2 | Composition 3 | Composition 4 |
|---|---|---|---|---|
| First Aliphatic Alcohol | 345 | 345 | 345 | 345 |
| Second Aliphatic Alcohol | 1380 | 1380 | 1380 | 1380 |
| Metal Catalyst | 20 | 20 | 20 | 20 |
| Ethylene Oxide | 2426 | 2831 | 3235 | 3640 |
| Weight Percent of First Aliphatic Alcohol | 20 | 20 | 20 | 20 |
| Weight Percent of Second Aliphatic Alcohol | 80 | 80 | 80 | 80 |
| Moles of Ethylene Oxide Added to Reaction | 6 | 7 | 8 | 9 |
| Cloud Point ° C. (1% Aq) | 29 | 35.6 | 51.7 | 64.5 |
| HLB | 11.7 | 12.5 | 13.1 | 13.6 |

| Components | Composition 5 | Composition 6 | Composition 7 | Composition 8 |
|---|---|---|---|---|
| First Aliphatic Alcohol | 345 | 345 | 345 | 825 |
| Second Aliphatic Alcohol | 1380 | 1380 | 1380 | 825 |
| Metal Catalyst | 20 | 20 | 20 | 18 |
| Ethylene Oxide | 4044 | 4448 | 4853 | 2469 |
| Weight Percent of First Aliphatic Alcohol | 20 | 20 | 20 | 50 |
| Weight Percent of Second Aliphatic Alcohol | 80 | 80 | 80 | 50 |
| Moles of Ethylene Oxide Added to Reaction | 10 | 11 | 12 | 6 |
| Cloud Point (1% Aq) | 73.9 | 81.2 | 89 | 2 |
| HLB | 14.1 | 14.5 | 14.8 | 12 |

| Components | Composition 9 | Composition 10 | Composition 11 | Composition 12 |
|---|---|---|---|---|
| First Aliphatic Alcohol | 825 | 825 | 825 | 825 |
| Second Aliphatic Alcohol | 825 | 825 | 825 | 825 |
| Metal Catalyst | 18 | 18 | 18 | 18 |
| Ethylene Oxide | 2880 | 3292 | 3703 | 4115 |
| Weight Percent of First Aliphatic Alcohol | 50 | 50 | 50 | 50 |
| Weight Percent of Second Aliphatic Alcohol | 50 | 50 | 50 | 50 |
| Moles of Ethylene Oxide Added to Reaction | 7 | 8 | 9 | 10 |
| Cloud Point (1% Aq) | 37.6 | 46.3 | 60.5 | 67.6 |
| HLB | 12.8 | 13.4 | 13.9 | 14.3 |

| Components | Composition 13 | Composition 14 | Composition 15 | Composition 16 |
|---|---|---|---|---|
| First Aliphatic Alcohol | 825 | 825 | 1260 | 1260 |
| Second Aliphatic Alcohol | 825 | 825 | 315 | 315 |
| Metal Catalyst | 18 | 18 | 18 | 18 |
| Ethylene Oxide | 4526 | 4937 | 2516 | 2936 |
| Weight Percent of First Aliphatic Alcohol | 50 | 50 | 80 | 80 |
| Weight Percent of Second Aliphatic Alcohol | 50 | 50 | 20 | 20 |
| Moles of Ethylene Oxide Added to Reaction | 11 | 12 | 6 | 7 |
| Cloud Point (1% Aq) | 76.2 | 83.3 | 2 | 15 |
| HLB | 14.7 | 15 | 12.3 | 13.1 |

TABLE 1-continued

| Components | Composition 17 | Composition 18 | Composition 19 | Composition 20 | Composition 21 |
|---|---|---|---|---|---|
| First Aliphatic Alcohol | 1260 | 1260 | 1260 | 1260 | 1260 |
| Second Aliphatic Alcohol | 315 | 315 | 315 | 315 | 315 |
| Metal Catalyst | 18 | 18 | 18 | 18 | 18 |
| Ethylene Oxide | 3355 | 3775 | 4194 | 4613 | 5033 |
| Weight Percent of First Aliphatic Alcohol | 80 | 80 | 80 | 80 | 80 |
| Weight Percent of Second Aliphatic Alcohol | 20 | 20 | 20 | 20 | 20 |
| Moles of Ethylene Oxide Added to Reaction | 8 | 9 | 10 | 11 | 12 |
| Cloud Point (1% Aq) | 43.4 | 53.6 | 61.7 | 72.5 | 77.8 |
| HLB | 13.7 | 14.2 | 14.6 | 14.9 | 15.3 |

The First Aliphatic Alcohol includes 2-propylheptanol, commercially available from BASF Corporation of Florham Park, N.J. under the trade name of Lutensol® PH-2.

The Second Aliphatic Alcohol includes a mixture of 1-dodecanol, 1-tridecanol, and 1-tetradecanol, commercially available from Proctor and Gamble of Cincinnati, Ohio under the trade name of Fatty Alcohol CO-1214 CNO, commercially available from Henkel KGaA of Düsseldorf, Germany under the trade name of Lorol® 3333, commercially available from Cognis Corp. USA of Cincinnati, Ohio under the trade name of C12-14 A, and commercially available from United Coconut Chemicals, Inc. of the Philippines under the trade name of Philcohol 1216.

The Metal Catalyst is a 45% by weight aqueous solution of potassium hydroxide.

After formation, samples of each of the Compositions 1-21, in addition to samples of Comparative Compositions 1-7, are independently added to four different I&I cleaning formulations (Cleaning Formulations 1-4) and these combinations are evaluated for Percent Cleaning. The Comparative Compositions 1-7 are not formed according to the instant invention and do not include amounts of a polyalkylene glycol in excess of three percent by weight.

The Comparative Composition 1 includes a blend of 7 mole ethylene oxide adducts of alcohols having from 12 to 14 carbon atoms and is commercially available from BASF Corporation of Wyandotte, Mich. under the trade name of Lutensol® A 65 N Surfactant.

The Comparative Composition 2 includes an 8 mole ethylene oxide adduct of 2-propylheptanol and is commercially available from BASF Corporation of Wyandotte, Mich. under the trade name of Lutensol® XP 80 Surfactant.

The Comparative Composition 3 includes a 9-mole ethylene oxide adduct of nonylphenol and is commercially available from BASF Corporation of Wyandotte, Mich. under the trade name of Lutensol® NP-9 Surfactant.

The Comparative Composition 4 includes a mixture of ethoxylates of $C_9$-$C_{11}$ and $C_{14}$-$C_{15}$ is commercially available from Tomah Products, Inc. of Milton, Wis. under the trade name of Tomadol® 900. The Tomadol® 900 does not include an amount of polyethylene glycol in excess of three percent by weight.

The Comparative Composition 5 includes 80% by weight of a 7 mole ethylene oxide adduct of 2-propylheptanol that is commercially available from BASF Corporation of Wyandotte, Mich. under the trade name of Lutensol® XP 70 Surfactant and 20% by weight of the Comparative Composition 1.

The Comparative Composition 6 includes 50% by weight of Lutensol® XP 70 Surfactant and 50% by weight of the Comparative Composition 1.

The Comparative Composition 7 includes 20% by weight of Lutensol® XP 70 Surfactant and 80% by weight of the Comparative Composition 1.

Cleaning Formulation 1 includes 1% by weight of one of Compositions 1-21 or one of the Comparative Compositions 1-7, 6% by weight of dipropylene glycol methyl ether, 5% by weight of a 50% by weight aqueous solution of NaOH, 3% by weight of Trilon® M, commercially available from BASF Corporation of Wyandotte, Mich., 3% by weight of a 40% by weight aqueous solution of sodium xylene sulfonate, and a balance of water.

Cleaning Formulation 2 includes 2% by weight of one of Compositions 1-21 or one of the Comparative Compositions 1-7, 6% by weight of dipropylene glycol methyl ether, 5% by weight of a 50% by weight aqueous solution of NaOH, 3% by weight of Trilon® M, commercially available from BASF Corporation of Wyandotte, Mich., 3% by weight of a 40% by weight aqueous solution of sodium xylene sulfonate, and a balance of water.

Cleaning formulation 3 includes 1% by weight of one of Compositions 1-21 or one of the Comparative Compositions 1-7, 1% by weight of a linear alkyl benzenesulfonate sodium salt, 8% by weight of sodium meta silicate, 6% by weight of EDTA, 1% by weight of a 50% by weight solution of NaOH, 6.5% by weight of sodium xylene sulfonate, and a balance of water.

Cleaning formulation 4 includes 4% by weight of one of Compositions 1-21 or one of the Comparative Compositions 1-7, 1% by weight of a linear alkyl benzenesulfonate sodium salt, 8% by weight of sodium meta silicate, 6% by weight of EDTA, 1% by weight of a 50% by weight solution of NaOH, 6.5% by weight of sodium xylene sulfanate, and a balance of water.

After the samples of the Compositions 1-21 and the Comparative Compositions 1-7 are added to the Cleaning Formulations 1 to 4, samples of each of the various Cleaning Formulations 1 and 2 are evaluated for Average Percent Cleaning in pour applications after each has been applied to soiled 4×6 inch vinyl tiles. The Average Percent Cleaning is determined using reflectance measurements of the tiles, according to ASTM 4488-95. Reflectance measurements of the tiles are determined using a reflectometer commercially available from X-Rite Asia Pacific Ltd. under the trade name of Colormaster. The reflectance measurements of the tiles are taken in three conditions, "Before Soiling", "After Soiling", and "After Cleaning". Specifically, an average of four reflectance measurements is determined for each individual tile, in each of the three conditions. The averages from each condition, from each of the four tiles, are subsequently averaged themselves to produce aggregate averages from each of the three conditions. These aggregate averages are used in calculations of Average Percent Cleaning, first introduced above and as set forth in Table 2 below. The Average Percent Cleaning measurements, relative to the Cleaning Formulations 1 and 2 and pour applications, are calculated as: {[(average reflectance "After Cleaning")–(average reflectance "After Soiling")]÷ [(average reflectance "Before Soiling")–(average reflectance "After Soiling")]}×100. Higher Average Percent Cleaning measurements indicate greater degrees of cleaning ability.

Initially, the reflectance of the clean tiles, i.e., the reflectance of the tiles "Before Soiling", is determined. Subsequently, the tiles are soiled with a First Soil Composition. The First Soil Composition includes a mixture of 50 grams of paint thinner, 4 grams of vegetable oil, 10 grams of mineral oil, 10 grams of clay, and 4.5 grams of graphite powder. After the tiles are soiled, the tiles are heated to 50° C. for 24 hours after which any excess of the First Soil Composition is wiped from the tiles. After the excess First Soil Composition is wiped from the tiles, the "After Soiling" reflectance of each of the tiles is determined.

To clean the tiles in these pour applications, a cellulose sponge is installed on a Gardner Scrubber. 5 ml of one of the various Cleaning Formulations 1 or 2 is deposited on the sponge and contacted with the tiles. The Gardner Scrubber is then cycled 20 times. After 20 cycles, an additional 5 ml of the respective Cleaning Formulation 1 or 2 is re-deposited on the cleaning pad and the 20 cycles are repeated. After cleaning using the Gardener Scrubber, the "After Cleaning" reflectance of each of the tiles is determined. Upon determination and averaging of each of the "Before Soiling", "After Soiling", and "After Cleaning" reflectance values for the tiles, the Average Percent Cleaning measurements are calculated and set forth in Table 2 below.

TABLE 2

Average Percent Cleaning

|  | Cleaning Formulation 1 | Cleaning Formulation 2 |
|---|---|---|
| Composition 1 | 35.79 | 75.34 |
| Composition 2 | 23.65 | 78.46 |
| Composition 3 | 59.9 | 74.05 |
| Composition 4 | 47.2 | 68.32 |
| Composition 5 | 33.84 | 69.4 |
| Composition 6 | 18.86 | 71.06 |
| Composition 7 | 18.14 | 66.77 |
| Composition 8 | 51.75 | 55.22 |
| Composition 9 | 35.78 | 76.22 |
| Composition 10 | 31.81 | 64.13 |
| Composition 11 | 43.31 | 62.87 |
| Composition 12 | 22.16 | 65.17 |
| Composition 13 | 25.75 | 62.95 |
| Composition 14 | 31.9 | 62.95 |
| Composition 15 | 48.32 | 56.14 |
| Composition 16 | 49.28 | 74.7 |
| Composition 17 | 45.25 | 78.77 |
| Composition 18 | 55.24 | 70.02 |
| Composition 19 | 28.41 | 66.96 |
| Composition 20 | 21.59 | 63.86 |
| Composition 21 | 25.86 | 61.7 |
| Comparative Composition 1 | 29.38 | 62.27 |
| Comparative Composition 2 | 26.4 | 50.4 |
| Comparative Composition 3 | 36.0 | 67.6 |
| Comparative Composition 4 | 54.6 | 70.5 |
| Comparative Composition 5 | 49.3 | 70.6 |
| Comparative Composition 6 | 49.3 | 72.7 |
| Comparative Composition 7 | 47.6 | 66.6 |

Samples of each of the Cleaning Formulations 3 and 4, each including one of the Compositions 1-21 or one of the Comparative Compositions 1-7, are evaluated for Average Percent Cleaning in spray applications through calculation of an average mass of soil removed from four aluminum coupons after soiling and cleaning. Specifically, the aluminum coupons are cleaned, weighed, and soiled with approximately one gram of a Second Soil Composition. The Second Soil Composition includes 50 grams of dirty motor oil, i.e., motor oil that has been previously used in an engine, combined with 50 grams of bandy black clay. After soiling with the Second Soil Composition, the aluminum coupons are placed in an oven at 65° C. for 24 hours to remove excess water. Subsequently, single aluminum coupons are sprayed at 45 psi for 30 seconds with a sample of one of the various Cleaning Formulations 3 or 4 while rotating at ½ revs/second speed in a spray box. After spraying, the aluminum coupons are rinsed with 100 ml of deionized water and heated for 2 hours at 65° C. to remove excess water. The aluminum coupons are then weighed to determine an amount of the Second Soil Composition removed. The amounts of the Second Soil Composition removed from the four individual coupons are then averaged and used to calculate the Average Percent Cleaning in spray applications, as first introduced above and as set forth in Table 3 below. The Average Percent Cleaning measurements for spray applications, relative to the Cleaning Formulations 3 and 4, are calculated as: [(average amount of soil removed (g)÷(average amount of soil added)]×100. Higher Average Percent Cleaning measurements indicate greater degrees of cleaning ability.

TABLE 3

Average Percent Cleaning

|  | Cleaning Formulation 3 | Cleaning Formulation 4 |
|---|---|---|
| Composition 1 | 35.62 | 48.25 |
| Composition 2 | 35.82 | 59.5 |
| Composition 3 | 38.16 | 62.3 |
| Composition 4 | 35.68 | 72.6 |
| Composition 5 | 37.9 | 61.2 |
| Composition 6 | 37.1 | 47.9 |
| Composition 7 | 39.1 | 47.5 |
| Composition 8 | 23.1 | 52 |
| Composition 9 | 35.62 | 71.1 |
| Composition 10 | 42.54 | 73.3 |
| Composition 11 | 35.06 | 69.42 |
| Composition 12 | 37.5 | 52.3 |
| Composition 13 | 65.23 | 52.8 |
| Composition 14 | 60.07 | 52.5 |
| Composition 15 | 25.9 | 80.8 |
| Composition 16 | 36.29 | 99.5 |
| Composition 17 | 32.5 | 99.3 |
| Composition 18 | 44.56 | 98.6 |

TABLE 3-continued

Average Percent Cleaning

| | Cleaning Formulation 3 | Cleaning Formulation 4 |
|---|---|---|
| Composition 19 | 60.93 | 72.3 |
| Composition 20 | 39.3 | 75 |
| Composition 21 | 37.5 | 74.3 |
| Comparative Composition 1 | 30 | 55.8 |
| Comparative Composition 2 | 29.9 | 70.5 |
| Comparative Composition 3 | 66.87 | 80.2 |
| Comparative Composition 4 | 33.41 | 61.2 |
| Comparative Composition 5 | 40.3 | 90.1 |
| Comparative Composition 6 | 35 | 68.1 |
| Comparative Composition 7 | 35 | 75 |

As shown in Tables 2 and 3, the Compositions of the instant invention are used to effectively clean the vinyl tiles when included in Cleaning Formulations 1 and 2 in bucket dilutable applications and effectively clean the aluminum coupons when included in Cleaning Formulations 3 and 4 in spray applications. In addition to being able to effectively clean the vinyl tiles and aluminum coupons in both pour and spray applications, respectively, the Compositions of the instant invention are also biodegradable and therefore may reduce a possibility of pollution and formation of environmental hazards when used.

Additionally, Amounts of Wetting of Compositions 3 and 18 and Comparative Compositions 1, 3, and 4 are determined by coating a 4×6 inch vinyl tile with a lime soap soil produced according to CSPA DCC-16, using a contact angle goniometer equipped with a video camera for measurement. An 0.5 μl drop of each of the Compositions 3 and 18 and Comparative Compositions 1, 3, and 4, present at approximately 500 ppm in water, is placed on the vinyl tile and measured for contact angle after 0.5, 1, 2, 4, 6, 8, 10, 20, 30, 40, and 50, seconds. As is known in the art, greater degrees of contact angles indicate decreased Amounts of Wetting due to the decreased dispersion of the drops on the tiles. The contact angle measurements are set forth in Table 4 below.

TABLE 4

| | Composition 3 | Composition 18 | Comparative Composition 1 | Comparative Composition 3 | Comparative Composition 4 |
|---|---|---|---|---|---|
| 0.5 Seconds | 73.8 | 55.5 | 76.8 | 83.3 | 55.4 |
| 1 Second | 71.2 | 52.9 | 75.1 | 80.7 | 52.9 |
| 2 Seconds | 67.1 | 50.5 | 71 | 77.8 | 49.5 |
| 4 Seconds | 64.6 | 48.1 | 68 | 75.2 | 48.2 |
| 6 Seconds | 62.8 | 47.2 | 63 | 73.6 | 47.1 |
| 8 Seconds | 61.2 | 45.6 | 59.9 | 70.9 | 46.1 |
| 10 Seconds | 60.2 | 44.9 | 59.6 | 71 | 44.9 |
| 20 Seconds | 55.7 | 41.4 | 54.4 | 66.1 | 43.7 |
| 30 Seconds | 53.2 | 39.2 | 52 | 63.8 | 39.2 |
| 40 Seconds | 51.1 | 37.3 | 51.7 | 60.3 | 38.5 |
| 50 Seconds | 49.5 | 35.8 | 50.2 | 58.7 | 41.3 |

As shown above in Table 4, the Compositions of the instant invention generally exhibit increased Amounts of Wetting, as compared to the Comparative Compositions. The increased Amounts of Wetting indicate that the Compositions of the instant invention make more complete contact with the soil on the vinyl tiles than the Comparative Compositions and therefore interact more completely with dirt and grease, leading to increased cleaning ability. Specifically, it is believed that increased wetting contributes to increased cleaning effectiveness and increased Average Percent Cleaning by the Compositions of the instant invention.

The invention has been described in an illustrative manner, and it is to be understood that the terminology which has been used is intended to be in the nature of words of description rather than of limitation. Obviously, many modifications and variations of the present invention are possible in light of the above teachings, and the invention may be practiced otherwise than as specifically described.

What is claimed is:

1. A surfactant composition comprising:
A. a first surfactant of the general formula;

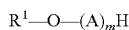

wherein $R^1$ is an aliphatic hydrocarbon having from 8 to 11 carbon atoms, A is an alkyleneoxy group having from 2 to 5 carbon atoms, and m is a positive number;
B. a second surfactant of the general formula;

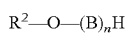

wherein $R^2$ is an aliphatic hydrocarbon having from 12 to 14 carbon atoms, B is an alkyleneoxy group having from 2 to 5 carbon atoms, and n is a positive number; and
C. a polyalkylene glycol present in an amount of from 3 to 20 parts by weight per 100 parts by weight of said surfactant composition.

2. A surfactant composition as set forth in claim 1 wherein said polyalkylene glycol is further defined as a polyethylene glycol.

3. A surfactant composition as set forth in claim 2 wherein said polyethylene glycol has a number average molecular weight of from 600 to 800 g/mol.

4. A surfactant composition as set forth in claim 3 wherein said polyethylene glycol is present in an amount of from 8 to 10 parts by weight per 100 parts by weight of said surfactant composition.

5. A surfactant composition as set forth in claim 1 wherein R1 is an aliphatic hydrocarbon having 10 carbon atoms.

6. A surfactant composition as set forth in claim 5 wherein said aliphatic hydrocarbon having 10 carbon atoms is further defined as a 2-propylheptane moiety.

7. A surfactant composition as set forth in claim 1 wherein A is further defined as an ethyleneoxy group.

8. A surfactant composition as set forth in claim 7 wherein m is a number of from 5 to 12.

9. A surfactant composition as set forth in claim 1 wherein said aliphatic hydrocarbon having from 8 to 11 carbon atoms has an average degree of branching of zero.

10. A surfactant composition as set forth in claim 1 wherein said aliphatic hydrocarbon having from 8 to 11 carbon atoms has an average degree of branching of greater than zero.

11. A surfactant composition as set forth in claim 1 wherein said first surfactant is present in an amount of from 15 to 75 parts by weight per 100 parts by weight of said composition.

12. A surfactant composition as set forth in claim 1 wherein R2 is an aliphatic hydrocarbon having 12 carbon atoms.

13. A surfactant composition as set forth in claim 12 wherein said aliphatic hydrocarbon having 12 carbon atoms is further defined as a dodecane moiety.

14. A surfactant composition as set forth in claim 1 wherein B is further defined as an ethyleneoxy group.

15. A surfactant composition as set forth in claim 14 wherein n is a number of from 5 to 12.

16. A surfactant composition as set forth in claim 1 wherein said aliphatic hydrocarbon having from 12 to 14 carbon atoms has an average degree of branching of zero.

17. A surfactant composition as set forth in claim 1 wherein said second surfactant is present in an amount of from 15 to 75 parts by weight per 100 parts by weight of said composition.

18. A surfactant composition as set forth in claim 1 having a cloud point of From 40 to 80° C.

19. A surfactant composition as set forth in claim 1 having a hydrophilic lipophilic balance of from 7 to 15 as determined by the Griffin method.

20. A surfactant composition as set forth in claim 1 having a critical micelle concentration of from 0.05 to 0.5, g/L.

21. A surfactant composition as set forth in claim 1 that is a liquid.

22. A surfactant composition as set forth in claim 1 that is a solid.

23. A surfactant composition as set forth in claim 1 having a pH of from 6 to 7.

24. A surfactant composition as set forth in claim 1 consisting essentially of said first surfactant, said second surfactant, and said polyalkylene glycol.

25. A surfactant composition as set forth in claim 24 wherein R1 is a 2-propylheptane moiety, A is an ethyleneoxy group, m is a number of from 5 to 12, R2 is a dodecane moiety, B is an ethyleneoxy group, n is an number of from 5 to 12, and said polyalkylene glycol is further defined as a polyethylene glycol having a number average molecular weight of from 600 to 800 g/mol.

26. A cleaning formulation having a pH of greater than 10 and comprising the surfactant composition as set forth in claim 1.

27. A method of forming a surfactant composition comprising a first surfactant of the general formula $R^1$—O—(A)$_m$H wherein R1 is an aliphatic hydrocarbon having from 8 to 11 carbon atoms, A is an alkyleneoxy group having from 2 to 5 carbon atoms, and m is positive number, a second surfactant of the general formula $R^2$—O—(B)$_n$H wherein $R^2$ is an aliphatic hydrocarbon having from 12 to 14 carbon atoms, B is an alkyleneoxy group having from 2 to 5 carbon atoms, and n is a positive number, and a polyalkylene glycol present in an amount of from 3 to 20 parts by weight per 100 parts by weight of the surfactant composition, said method comprising the steps of:
   A. alkoxylating a first aliphatic alcohol having from 8 to 11 carbon atoms in the presence of a catalyst to form the first surfactant and the polyalkylene glycol in situ;
   B. alkoxylating a second aliphatic alcohol having from 12 to 14 carbon atoms in the presence of the catalyst to form the second surfactant and the polyalkylene glycol in situ; and
   C. combining the first surfactant, the second surfactant, and the polyalkylene glycol to form the surfactant composition.

28. A method as set forth in claim 27 wherein the steps of alkoxylating the first alcohol and alkoxylating the second alcohol are completed simultaneously.

29. A method as set forth in claim 27 wherein the polyalkylene glycol is further defined as a polyethylene glycol.

30. A method as set forth in claim 29 wherein the polyethylene glycol has a number average molecular weight of from 600 to 800 g/mol.

31. A method as set forth in claim 30 wherein the polyethylene glycol is present in an amount of from 8 to 10 parts by weight per 100 parts by weight of the surfactant composition.

32. A method as set forth in claim 27 wherein R1 is further defined as a 2- propylheptane moiety.

33. A method as set forth in claim 27 wherein A is further defined as an ethyleneoxy group.

34. A method as set forth in claim 27 wherein m is a number of from 5 to 12.

35. A method as set forth in claim 27 wherein the aliphatic hydrocarbon having from 8 to 11 carbon atoms has an average degree of branching of zero.

36. A method as set forth in claim 27 wherein the aliphatic hydrocarbon having from 8 to 11 carbon atoms has an average degree of branching of greater than zero.

37. A method as set forth in claim 27 wherein the first surfactant is present in an amount of from 15 to 75 parts by weight per 100 parts by weight of the surfactant composition.

38. A method as set forth in claim 27 wherein R2 is further defined as a dodecane moiety.

39. A method as set forth in claim 27 wherein B is further defined as an ethyleneoxy group.

40. A method as set forth in claim 27 wherein n is a number of from 5 to 12.

41. A method as set forth in claim 27 wherein the second surfactant is present in an amount of from 15 to 75 parts by weight per 100 parts by weight of the surfactant composition.

42. A method as set forth in claim 27 wherein the catalyst is a metal catalyst.

* * * * *